(12) United States Patent
Hamaoki

(10) Patent No.: US 8,404,434 B2
(45) Date of Patent: *Mar. 26, 2013

(54) METHOD FOR DETERMINING DEGREE OF NEGATIVE EFFECT OF MACROPHAGES ON VERTEBRATE

(75) Inventor: Masaru Hamaoki, Choshi (JP)

(73) Assignee: Yamasa Corporation, Chiba (JP)

( * ) Notice: Subject to any disclaimer, the term of this patent is extended or adjusted under 35 U.S.C. 154(b) by 107 days.

This patent is subject to a terminal disclaimer.

(21) Appl. No.: 12/656,809

(22) Filed: Feb. 17, 2010

(65) Prior Publication Data

US 2010/0151585 A1 Jun. 17, 2010

Related U.S. Application Data

(62) Division of application No. 11/699,018, filed on Jan. 29, 2007, now Pat. No. 7,687,231.

(30) Foreign Application Priority Data

Jan. 30, 2006 (JP) ................................. 2006-021073

(51) Int. Cl.
*G01N 33/53* (2006.01)
(52) U.S. Cl. ............................................. 435/4; 453/7.1
(58) Field of Classification Search .................. None
See application file for complete search history.

(56) References Cited

FOREIGN PATENT DOCUMENTS

| EP | 1 610 127 | 12/2005 |
|---|---|---|
| JP | 3709078 | 10/2005 |

OTHER PUBLICATIONS

Hiramatsu et al., Clin. Cancer Res., vol. 11, Apr. 18, 2005, pp. 2986-2990.*
Kawakita et al., J. Biochem., vol. 139, Mar. 2006, pp. 315-322.*
Yamaguchi et al., Dig. Liver Disease, vol. 37, Dec. 15, 2004, pp. 190-194.*
Akemi et al., Rinsho byori. The Japanese journal of clinical pathology, vol. 52, Apr. 2004, pp. 328-331 (Abstract Only).*
Yu et al., "Inflammatory and Immune Cells in Tumor Angiogenesis and Arteriogenesis," Breast Cancer Research, vol. 5, pp. 83-88, (2003).
Hiramatsu et al., "Diagnostic and Prognostic Usefulness of $N^1$, $N^8$-Diacetylspermidine and $N^1$, $N^{12}$-Diacetylspermine in Urine as Novel Markers of Malignancy," J. Cancer Res. Clin. Oncol., vol. 123, pp. 539-545, (1997).
Hamaoki et al., "Two Enzyme-Linked Immunosorbent Assay (ELISA) Systems for $N^1$, $N^8$-Diacetylspermidine and $N^1$, $N^{12}$-Diacetylspermine Using Monoclonal Antibodies," J. Biochem., vol. 132, pp. 783-788, (2002).
Hamaoki et al., "Host Macrophages Produce Diacetylspermine Related with Tumorigenesis," Cancer Letters, vol. 243, pp. 128-134, (2006).
"Angiogenic Inhibitor", *Rinsho-Kensa*, vol. 44, No. 13, Dec. 2000, pp. 1627-1633 [with English translation].

* cited by examiner

*Primary Examiner* — Jeffrey Stucker
*Assistant Examiner* — Stephen Gucker
(74) *Attorney, Agent, or Firm* — Wenderoth, Lind & Ponack, L.L.P.

(57) ABSTRACT

The present invention provides a method for determining the degree of macrophage-associated negative effects on a vertebrate including a human, the method including assaying diacetylpolyamine contained in a sample collected from the vertebrate. According to the method of the present invention, metabolic conditions of macrophages can be monitored, and the degree of macrophage-associated negative effects on a vertebrate (including a human) can be determined. Specifically, the present invention can predict, through assay of diacetylpolyamine, pathological condition which is considered a macrophage-related disease; e.g., recurrence of cancer or malignant tumor, or infiltration or activation of cancer or malignant tumor cells; denaturation or degeneration of neurons associated with Alzheimer's disease; or onset or progression of an autoimmune disease (e.g., rheumatism or Crohn's disease) or arteriosclerosis. Therefore, the present invention is very useful for clinical tests.

3 Claims, 1 Drawing Sheet

METHOD FOR DETERMINING DEGREE OF NEGATIVE EFFECT OF MACROPHAGES ON VERTEBRATE

This application is a divisional of application Ser. No. 11/699,018, filed Jan. 29, 2007 now U.S. Pat. No. 7,687,231.

BACKGROUND OF THE INVENTION

1. Field of the Invention

The present invention relates to a method for determining the degree of negative effects of macrophages on a vertebrate (including a human), the method including assaying diacetylpolyamine contained in a sample collected from the vertebrate.

2. Background Art

As has been said, accumulation of macrophages in a cancerous area of a subject suffering cancer is correlated with the malignancy of the cancer, and macrophages participate in inflammatory response or tissue reconstruction in the affected area (Breast Cancer Res., 2003, 5: 83-88).

Understanding the state of macrophages specific to such inflammatory response or tissue reconstruction would be useful for determining the degree of progression of the disease or selecting a therapeutic method for the disease.

Hitherto, several factors produced by macrophages have been reported, but there has not yet been reported a marker which directly reflects metabolic conditions of macrophages; in particular, negative effects of macrophages on a patient.

Recently, diacetylpolyamines (e.g., diacetylspermine and diacetylspermidine) have become of interest as cancer-specific markers, and specific assays therefor have been reported (see, for example, Japanese Patent No. 3709078, WO 2004/81569, J. Cancer Res. Clin. Oncol., 123 (1997), 539-545, and J. Biochem. (Tokyo), 132 (2002), 783-788).

Such diacetylpolyamines have been considered to be produced by cancer cells per se. However, studies have not yet elucidated the mechanism of diacetylpolyamine production, the relation between diacetylpolyamine and cancer progression, and the relation between diacetylpolyamine production and macrophages.

As described above, there has not yet been reported a marker which directly reflects metabolic conditions of macrophages; in particular, negative effects of macrophages on a patient. Therefore, such a specific marker, if developed, would be employed as a very useful diagnostic marker for determining, for example, the degree of infiltration or malignancy of cancer, or for predicting the likelihood of cancer recurrence.

SUMMARY OF THE INVENTION

In view of the foregoing, an object of the present invention is to develop a marker which directly reflects negative effects of macrophages on a patient.

During the course of studies on the mechanism of production of diacetylpolyamines in cancer cells, quite unexpectedly, the present inventor has found that diacetylpolyamines are not produced by cancer cells, but by macrophages. The present inventor has conducted further studies on the basis of this finding, and as a result has found that production of diacetylpolyamines by macrophages directly reflects metabolic conditions of macrophages; in particular, the degree of macrophage-associated negative effects on a vertebrate (including a human), and therefore there can be directly determined worsening of diseases, disorders, or other pathological conditions which are associated with macrophages or highly suspected of being associated with macrophages, including cancer, Alzheimer's disease, rheumatism, Crohn's disease, and arteriosclerosis. The present invention has been accomplished on the basis of this finding. Accordingly, the present invention provides the following.

(1) A method for determining the degree of macrophage-associated negative effects on a vertebrate including a human, the method comprising assaying diacetylpolyamine contained in a sample collected from the vertebrate.

(2) A method as described in (1) above, wherein the degree of macrophage-associated negative effects on a vertebrate including a human serves as an indicator which shows worsening of a macrophage-related disease, disorder, or pathological condition (3) A method as described in (1) above, wherein the degree of macrophage-associated negative effects on a vertebrate including a human serves as an indicator which shows recurrence of cancer or malignant tumor, or infiltration or activation of cancer or malignant tumor cells.

(4) A method as described in (1) above, wherein the degree of macrophage-associated negative effects on a vertebrate including a human serves as an indicator which shows denaturation or degeneration of neurons associated with neurological diseases such as Alzheimer's disease.

(5) A method as described in (1) above, wherein the degree of macrophage-associated negative effects on a vertebrate including a human serves as an indicator which shows onset or progression of an autoimmune disease such as rheumatism or Crohn's disease.

(6) A method as described in (1) above, wherein the degree of macrophage-associated negative effects on a vertebrate including a human serves as an indicator which shows onset or progression of arteriosclerosis.

(7) A method as described in (1) above, wherein the diacetylpolyamine is diacetylspermine and/or diacetylspermidine.

(8) A method as described in (1) above, wherein the level of diacetylpolyamine contained in the sample is measured through immunoassay.

(9) A method as described in (1) above, wherein the level of diacetylpolyamine contained in a sample from a patient is measured (which is called sample diacetylpolyamine level); levels of diacetylpolyamine contained in samples from healthy subjects are measured likewise to obtain a mean level (which is called reference diacetylpolyamine level); the thus-obtained sample diacetylpolyamine level and the reference diacetylpolyamine level are compared with each other; and, when the sample diacetylpolyamine level is higher than the reference level, the degree of negative effects of macrophages on the patient is determined to be high.

(10) A method of using diacetylpolyamine as a specific marker for determining the degree of macrophage-associated negative effects on a vertebrate including a human.

(11) A method as described in (10) above, wherein the environmental and metabolic conditions of macrophages in vivo are determined.

Through assay of diacetylpolyamine contained in a sample, the environmental and metabolic conditions of macrophages in vivo can be monitored, and the degree of macrophage-associated negative effects on a vertebrate (including a human) can be determined. Specifically, the present invention facilitates prediction, through assay of diacetylpolyamine, of a pathological condition which is considered a macrophage-related disease; e.g., recurrence of cancer or malignant tumor, or infiltration or activation of cancer or malignant tumor cells; denaturation or degeneration of neurons associated with Alzheimer's disease; or onset or progression of an autoimmune disease (e.g., rheumatism or Crohn's disease) or arteriosclerosis. Therefore, the present invention is very useful for clinical tests.

BRIEF DESCRIPTION OF THE DRAWINGS

In FIG. 2, black diamonds, black squares, black triangles, and the symbol "×" correspond to data when the number of cells is $1\times10^5$, $1.5\times10^5$, $2\times10^5$, or $2.5\times10^5$, respectively.

DETAILED DESCRIPTION OF PREFERRED EMBODIMENTS

Figure 1:
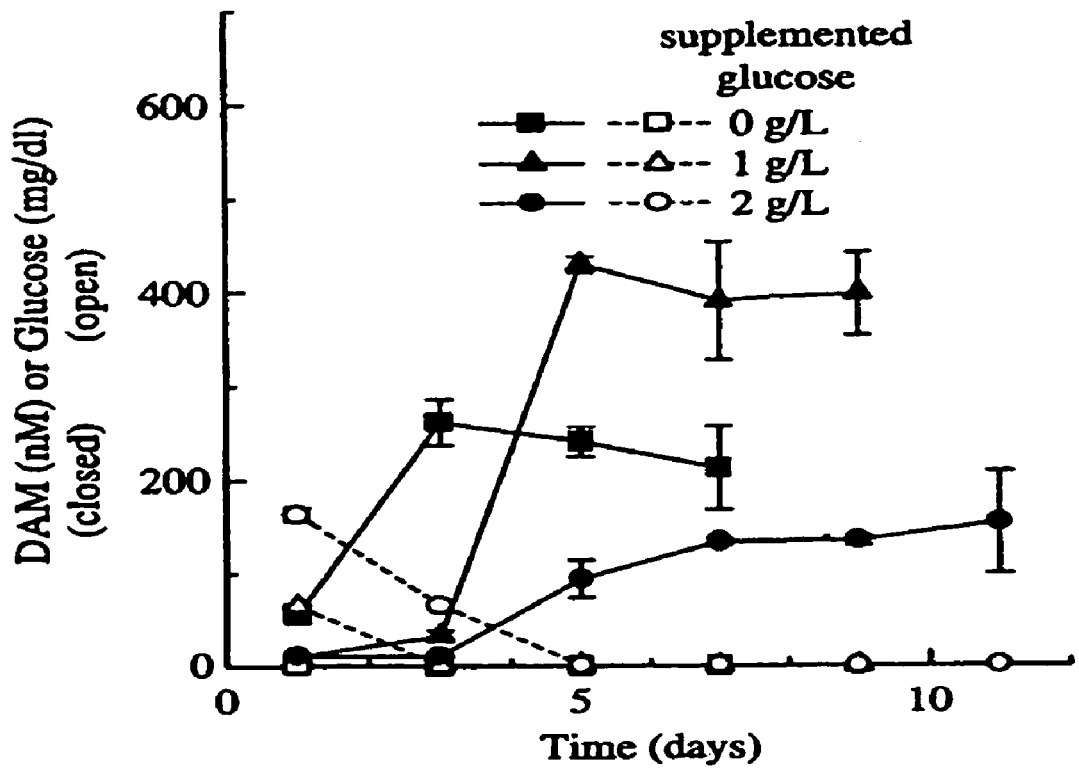
FIG. 1 is a graph in which glucose and diacetylspermine (DAM) levels are plotted against culture period of time (days).

As used herein, the term "diacetylpolyamine" refers to diacetylspermine and/or diacetylspermidine. Specific examples include $N^1,N^8$-diacetylspermidine and $N^1,N^{12}$-diacetylspermine.

As used herein, the term "macrophage-related disease" refers to a disease whose onset or progression is directly or indirectly associated with macrophages, or is suspected of being associated with macrophages. Specific examples of macrophage-related diseases include diseases caused by abnormal growth of cells (e.g., cancer and malignant tumor); neurological diseases caused by denaturation or degeneration of neurons (e.g., Alzheimer's disease); autoimmune diseases caused by immune dysfunction (e.g., rheumatism); and vascular diseases developed through deposition of cholesterol via receptors on macrophages (e.g., arteriosclerosis).

As used herein, the expression "negative effects" refers to effects or conditions which are undesirable to vertebrates (including a human). Macrophages, which are fundamentally essential for maintaining immune function of vertebrates (including a human), can cause physically undesirable effects (e.g., angiogenesis in cancer cells) on vertebrates (including a human) in response to environmental or metabolic conditions of macrophages in vivo. As used herein, such undesirable effects on vertebrates (including a human) are called "negative effects."

No particular limitation is imposed on the "sample" employed in the present invention, so long as the sample contains diacetylpolyamine. Specific examples of such a sample include urine and serum. In particular, a urine sample is preferably employed.

As used herein, the term "recurrence" refers to recurrence of a disease in an organ in which the disease has been originally developed, as well as to metastasis of the disease; i.e., development of the disease in another organ or tissue.

(A) Assay of Diacetylpolyamine

No particular limitation is imposed on the method for assaying diacetylpolyamine contained in a sample. Among various assays, immunoassay is particularly preferred, from the viewpoint of convenience. Immunoassay can be carried out through a specific procedure described in a known publication (e.g., Japanese Patent No. 3709078, WO 2004/81569, J. Cancer Res. Clin. Oncol., 123 (1997), 539-545, or J. Biochem. (Tokyo), 132 (2002), 783-788), which also describes reagents employed for immunoassay.

(B) Determination of the Degree of Macrophage-Associated Negative Effects

Diacetylpolyamine contained in a sample from a patient is assayed through the aforementioned method; the obtained diacetylpolyamine level is compared with a reference value as determined from diacetylpolyamine levels of samples from healthy subjects, the diacetylpolyamine levels being measured in a manner similar to that described above; and, when the diacetylpolyamine level of the patient sample is higher than the reference level obtained form the healthy subject samples, the degree of negative effects of macrophages on the patient is determined to be high.

As described below in the Examples section, increased production of diacetylpolyamines by macrophages indicates that macrophages in vivo are in hypoxic conditions, or conditions in which sugar (e.g., glucose) is depleted. Under such environmental and metabolic conditions, macrophages promote angiogenesis in cancer cells, and increase the degree of physical negative effects (e.g., recurrence of cancer, or infiltration or activation of cancer cells) on vertebrates (including a human).

This applies not only to the case of cancer, but to all macrophage-related diseases. The level of diacetylpolyamine is proportional to the degree of macrophage-associated negative effects. Therefore, when the level of diacetylpolyamine contained in a sample from a patient is measured, and the thus-measured diacetylpolyamine level is compared with the reference diacetylpolyamine level as determined on samples from healthy subjects, the degree of macrophage-associated negative effects on the patient can be determined.

EXAMPLES

The present invention will next be described in detail by way of Examples, which should not be construed as limiting the invention thereto.

(1) Relation Between Glucose Levels and Diacetylpolyamine Production in Macrophages Peritoneal macrophages collected from mice injected with thioglycollate were inoculated into a 96-well microplate ($1.25\times10^5$ cells/well), followed by culturing. In this case, cell culture was performed by use of RPMI 1640 medium containing 10% horse serum, the medium being supplemented with spermine (i.e., a raw material of diacetylpolyamine) (10 µM) and glucose (0, 1, or 2 g/L).

After completion of culturing, the levels of diacetylspermine and residual glucose contained in the medium were measured through a customary method. The results are shown in FIG. 1. As is clear from FIG. 1, diacetylspermine is produced in response to depletion of glucose.

(2) Relation Between Mitochondrial Activity and Diacetylpolyamine Production (i)

Dinitrophenol (DNP), which is a reagent called "uncoupler" that forcibly reduces the active potential of mitochondria, is added to a medium in an amount of 100 µM, followed by culturing for two days in a manner similar to that described above. After completion of culturing, diacetylspermine level was measured. The medium was supplemented with glucose in an amount of 2 g/L.

The results are shown in Table 1. As is clear from Table 1, even in the presence of glucose, diacetylspermine is produced through reduction of the active potential of mitochondria.

TABLE 1

|  | DNP absent | DNP present |
|---|---|---|
| Diacetylspermine (nM) | 13.2 | 61.8 |

(3) Relation Between Mitochondrial Activity and Diacetylpolyamine Production (ii)

Culturing was performed through an alternative approach for reducing mitochondrial activity. Specifically, in a manner similar to that described above, culturing was performed for one day in a medium supplemented with glucose (2 g/L) under hypoxic conditions (oxygen concentration=about 7% (v/v)) (control: oxygen concentration=21% (v/v)). After completion of culturing, diacetylspermine level was measured.

The results are shown in Table 2. As is clear from Table 2, even in the presence of glucose, diacetylspermine is produced through reduction of mitochondrial activity by a decrease in oxygen concentration.

TABLE 2

| | Oxygen 21% | Oxygen 7% |
|---|---|---|
| Diacetylspermine (nM) | 40.6 or less | 126.0 |

(4) Relation Between Mitochondrial Activity and Diacetylpolyamine Production (iii)

In order to examine the origin of acetyl CoA (i.e., a raw material of diacetylpolyamine), 1,2,3-benzyltricarboxylate (BTA), which is an inhibitor of a tricarboxylate carrier used for transportation of citrate from mitochondria to the cytoplasm, was added in an amount of 10 mM to a medium supplemented with no glucose, followed by measurement of diacetylspermine level.

The results are shown in Table 3. As is clear from Table 3, production of diacetylspermine is inhibited by BTA, which indicates that citrate transported from mitochondria to the cytoplasm is cleaved by (ATP-dependent) citrate lyase into acetyl CoA and oxaloacetate, and the resultant acetyl CoA is employed as a raw material of diacetylspermine.

TABLE 3

| | BTA absent | BTA present |
|---|---|---|
| Diacetylspermine (nM) | 150.9 | 43.0 |

(5) Relation Between Mitochondrial Activity and Diacetylpolyamine Production (iv)

In order to examine the quantitative relation between oxygen consumption rate and diacetylspermine production amount, cells were cultured under restricted oxygen supply with the number of cells and culture medium volume per well being varied, and diacetylspermine production amount was obtained. The culture medium employed was supplemented with lactate in place of glucose. At steady state, conceivably, lactate consumption rate corresponds to the rate of consumption thereof in the citric acid cycle, and is equal to the rate at which reduced nicotinamide adenine dinucleotide (NADH) produced in the cycle is oxidized by oxygen in the electron transport chain. For culturing, the number of cells was determined to be $1.0 \times 10^5$, $1.5 \times 10^5$, $2.0 \times 10^5$, or $2.5 \times 10^5$ per well, and the volume of a culture medium was determined to be 100, 150, 200, 250, or 300 µL per well. Diacetylspermine production amount was obtained through assay of the resultant supernatant on day 4 of culturing, on which production of diacetylspermine was completed.

Figure 2:
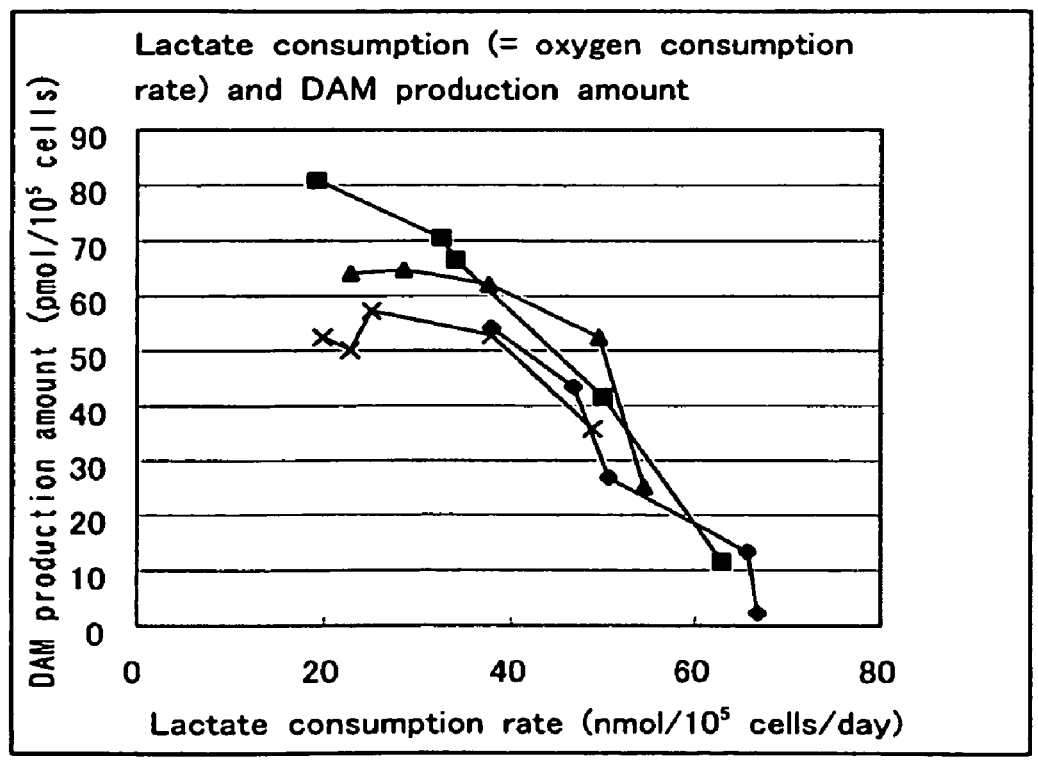
FIG. 2 is a graph in which diacetylspermine (DAM) level is plotted against lactate consumption rate (i.e., oxygen consumption rate).

The results are shown in FIG. 2. As is clear from FIG. 2, production of diacetylspermine is initiated when lactate consumption rate is lowered to a certain level or less due to a drop in oxygen concentration, and the amount of diacetylspermine produced is increased in accordance with a decrease in lactate consumption rate. As shown in FIG. 2, data points corresponding to the same cell count are connected by a line for the sake of convenience, but test data corresponding to different cell counts are almost overlapped. Therefore, conceivably, diacetylspermine production is not affected by the number of cells or the amount of a culture medium (i.e., no effect of cell-to-cell interaction or secreted factors); i.e., the factor determining the amount of diacetylspermine produced is only lack of oxygen, which is represented by a decrease in lactate consumption rate. In addition, since the amount of diacetylspermine produced is in almost linear relation with a decrease in lactate consumption rate, lack of oxygen in macrophages is considered to be "proportional" to the amount of diacetylspermine produced.

(6) Discussion

Mitochondria produce cellular energy (ATP) by oxidizing, with oxygen, NADH produced in the citric acid cycle in the mitochondrial matrix, and thus mitochondrial activity is considered to be represented by oxygen consumption rate. When mitochondrial activity is reduced; mitochondria cannot hold citrate. As described above, the amount of diacetylspermine produced, which serves as an indicator showing the amount of the thus-leaked citrate, is in linear relation with a reduction in mitochondrial activity; i.e., a decrease in oxygen consumption rate. Therefore, diacetylspermine serves as an indicator which shows that macrophages are in hypoxic conditions. As described above in (1), glucose depletion promotes production of diacetylspermine. Conceivably, this promotion is due to lack of oxygen through enhancement of the requirement for mitochondrial ATP production (i.e., oxygen requirement) as a result of no supply of ATP produced by glucose.

Conceivably, reduction of glucose level or oxygen concentration in vivo occurs at a site away from blood vessels or a necrotic portion. An increase in diacetylspermine level in a sample from a vertebrate (including a human) predicts the negative effects of macrophages on the vertebrate due to infiltration of macrophages in such a site, and reduction of mitochondrial activity. When macrophages, which have tissue reconstruction ability, are in hypoxic conditions (reduction of oxygen concentration is considered an angiogenesis-inducing factor), the cells are directly involved in angiogenesis, thereby causing recurrence of cancer or malignant tumor, or infiltration or activation of cancer or malignant tumor cells.

The method of the present invention is envisaged to greatly contribute to determination of therapeutic effects of cancer or malignant tumor, whose prognosis is greatly affected by angiogenesis, as well as to selection of therapeutic drugs for the disease. In addition to the case of cancer, the method is envisaged to contribute to development of therapeutic methods for diseases, disorders, or other pathological conditions which are associated with macrophages or highly suspected of being associated with macrophages (e.g., Alzheimer's disease, rheumatism, and arteriosclerosis), as well as to elucidation of the pathological and physiological mechanism of the diseases through determination of worsening of the diseases.

What is claimed is:

1. A method for determining if environmental and metabolic conditions of macrophages within the living body of a patient are either in hypoxic conditions or under conditions in which glucose is depleted, and therefore angiogenesis is promoted and cancer is recurring, or infiltration or activation of cancer cells has occurred, comprising:
    measuring the level of diacetylpolyamine contained in a macrophage sample collected from the patient to obtain a sample diacetylpolyamine level,
    measuring the levels of diacetylpolyamine contained in macrophage samples from healthy subjects to obtain a mean value and reference diacetylpolyamine level,
    comparing the sample diacetylpolyamine level with the reference diacetylpolyamine level, and
    when the sample diacetylpolyamine level is higher than the reference diacetylpolyamine level the environmental and metabolic conditions of macrophages within the living body of the patient are either in hypoxic conditions or under conditions in which glucose is depleted, and angiogenesis is promoted and cancer is recurring, or infiltration or activation of cancer cells has occurred.

2. The method as described in claim 1, wherein the diacetylpolyamine is diacetylspermine and/or diacetylspermidine.

3. The method as described in claim 1, wherein the levels of diacetylpolyamine contained in the macrophage samples are measured by immunoassay.

* * * * *